(12) United States Patent
Suzuki

(10) Patent No.: US 11,944,269 B2
(45) Date of Patent: Apr. 2, 2024

(54) ENDOSCOPE CONNECTOR AND ENDOSCOPE

(71) Applicant: OLYMPUS CORPORATION, Tokyo (JP)

(72) Inventor: Hiroya Suzuki, Akishima (JP)

(73) Assignee: OLYMPUS CORPORATION, Tokyo (JP)

(*) Notice: Subject to any disclaimer, the term of this patent is extended or adjusted under 35 U.S.C. 154(b) by 522 days.

(21) Appl. No.: 17/145,462

(22) Filed: Jan. 11, 2021

(65) Prior Publication Data

US 2021/0127954 A1    May 6, 2021

Related U.S. Application Data

(63) Continuation of application No. PCT/JP2018/026685, filed on Jul. 17, 2018.

(51) Int. Cl.
*A61B 1/00* (2006.01)
*A61B 1/04* (2006.01)
(Continued)

(52) U.S. Cl.
CPC ......... *A61B 1/00124* (2013.01); *H05K 9/006* (2013.01); *A61B 1/04* (2013.01);
(Continued)

(58) Field of Classification Search
CPC ............ A61B 1/00124; A61B 1/00114; H01R 13/2442; H01R 2201/12; H01R 13/648;
(Continued)

(56) References Cited

U.S. PATENT DOCUMENTS

| 4,820,201 A * | 4/1989 | Van Brunt ......... H01R 13/6588 |
| | | 439/607.3 |
| 2002/0098732 A1* | 7/2002 | Shimizu ............. A61B 1/00128 |
| | | 439/352 |
| 2012/0202385 A1 | 8/2012 | Miyagi et al. |
| 2014/0094656 A1 | 4/2014 | Matsukawa et al. |
| 2014/0184771 A1 | 7/2014 | Mazzetti et al. |

(Continued)

FOREIGN PATENT DOCUMENTS

| EP | 2478825 A1 | 7/2012 |
| JP | 2009-267123 A | 11/2009 |

(Continued)

OTHER PUBLICATIONS

International Search Report dated Sep. 4, 2018 issued in PCT/JP2018/026685.

*Primary Examiner* — Aaron B Fairchild
(74) *Attorney, Agent, or Firm* — Scully, Scott, Murphy & Presser, P.C.

(57) ABSTRACT

An endoscope connector includes: a plug including an electric contact configured to be electrically connected to an external medical apparatus, the plug being provided with a first substrate; a first frame electrically connected to the plug; a second frame electrically connected to the first frame, the second frame being made of metal; a first electric connection member electrically connected to the first substrate; a second electric connection member connected to the first electric connection member; a substrate unit including a second substrate and an electromagnetic shield member covering the second substrate, the electromagnetic shield member being made of metal; and an urging member configured to urge the substrate unit in a direction of the second frame, and to put the electromagnetic shield member into an electric conduction state by causing the electromagnetic shield member to abut on the second frame.

16 Claims, 4 Drawing Sheets

(51) Int. Cl.
  *H05K 9/00*  (2006.01)
  *A61B 1/06*  (2006.01)
  *H01R 13/24*  (2006.01)

(52) U.S. Cl.
  CPC ............ *A61B 1/06* (2013.01); *H01R 13/2442* (2013.01); *H01R 2201/12* (2013.01)

(58) Field of Classification Search
  CPC .............. H01R 13/658; H01R 13/6581; H01R 13/6585; H01R 13/6591; H01R 13/65912; H01R 13/65914; H01R 13/65917; H01R 13/6596; H01R 13/6597
  See application file for complete search history.

(56)        References Cited

U.S. PATENT DOCUMENTS

2014/0187060 A1      7/2014  Kubo
  2016/0353617 A1*    12/2016  Gimblet ................. H01B 11/22

FOREIGN PATENT DOCUMENTS

| JP | 2010-226001 A | 10/2010 |
| JP | 5507026 B1 | 5/2014 |
| JP | 2017-006162 A | 1/2017 |
| JP | 2017-006163 A | 1/2017 |
| JP | 6297227 B1 | 3/2018 |
| WO | WO 2011/052408 A1 | 5/2011 |
| WO | WO 2013/114661 A1 | 8/2013 |
| WO | WO 2014/083959 A1 | 6/2014 |
| WO | WO 2014/106059 A2 | 7/2014 |
| WO | WO 2017/208598 A1 | 12/2017 |

\* cited by examiner

ENDOSCOPE CONNECTOR AND ENDOSCOPE

CROSS REFERENCE TO RELATED APPLICATION

This application is a continuation application of PCT/JP2018/026685 filed on Jul. 17, 2018, the entire contents of which are incorporated herein by this reference.

BACKGROUND OF THE INVENTION

1. Field of the Invention

The present invention relates to an endoscope connector and an endoscope that are connected to an external apparatus such as a light source device.

2. Description of the Related Art

An endoscope device that is a medical apparatus is connected to a video processor, a light source device and the like that are peripheral apparatuses. Therefore, in the endoscope device, an endoscope connector that can be connected to the video processor, the light source device and the like in a detachable manner is arranged at an extension end of a signal cable.

Such an endoscope connector is disclosed in International Publication No. 2011/052408, for example. International Publication No. 2011/052408 discloses a technology of an endoscope connector that enhances assembly workability by securing a sufficient strength corresponding to a usage environment and in addition effectively securing a disposition space for incorporated components.

The endoscope connector houses a main-substrate configured to perform signal processing for an image sensor and an external medical apparatus, and falls under a medical apparatus, so that EMC conformity is required. Therefore, for meeting EMC conformity items for the medical apparatus, a conventional endoscope connector is required to have a configuration of suppressing emission levels of electric waves and electromagnetic fields or reducing influences of electric waves and electromagnetic fields from an exterior.

In the configuration of the conventional endoscope connector, a substrate shield made of metal and covering a single main-substrate and a signal wire connected to the main-substrate are connected to a metal frame having a large current-carrying capacity, and thereby, noise emission is suppressed. Furthermore, the conventional endoscope connector increases noise immunity by interposing a connector shield made of metal and having a shape for entirely covering a periphery of a signal wire connected to a substrate unit and the main-substrate.

In the conventional endoscope connector, a sub-substrate contained in a plug that is a connection portion to the external medical apparatus and the substrate unit attached to the metal frame connected to a plug portion are connected by a signal wire, and an endoscope connector in which the substrate unit is connected to the sub-substrate by a board-to-board (B to B) connector for reduction in parts count and simplification of assembly is known.

SUMMARY OF THE INVENTION

An endoscope connector in an aspect of the present invention includes: a plug configured to be connected to an external medical apparatus, the plug including an electric contact configured to be electrically connected to the external medical apparatus, the plug being provided with a first substrate to which the electric contact is electrically connected; a first frame electrically connected to the plug; a second frame electrically connected to the first frame, the second frame being made of metal; a first electric connection member electrically connected to the first substrate; a second electric connection member configured to be electrically connected to the first electric connection member; a substrate unit including a second substrate electrically connected to the second electric connection member and an electromagnetic shield member covering the second substrate, the electromagnetic shield member being made of metal; and an urging member configured to urge the substrate unit in a direction of causing the substrate unit to be close to the second frame, and to put the electromagnetic shield member into an electric conduction state by causing the electromagnetic shield member to abut on the second frame.

An endoscope connector in another aspect of the present invention includes: a first substrate configured to be electrically connected to an external medical apparatus; a first frame configured to be electrically connected to a ground of the external medical apparatus; a second frame electrically connected to the first frame; a first electric connection member electrically connected to the first substrate; a second electric connection member configured to be electrically connected to the first electric connection member; a substrate unit including a second substrate electrically connected to the second electric connection member and an electromagnetic shield member covering the second substrate; and an urging member configured to urge the substrate unit in a direction of causing the substrate unit to be close to the second frame, and to put the electromagnetic shield member into an electric conduction state by causing the electromagnetic shield member to abut on the second frame.

An endoscope in an aspect of the present invention includes an endoscope connector including: a plug configured to be connected to an external medical apparatus, the plug including an electric contact configured to be electrically connected to the external medical apparatus, the plug being provided with a first substrate to which the electric contact is electrically connected; a first frame electrically connected to the plug; a second frame electrically connected to the first frame, the second frame being made of metal; a first electric connection member electrically connected to the first substrate; a second electric connection member configured to be connected to the first electric connection member; a substrate unit including a second substrate electrically connected to the second electric connection member and an electromagnetic shield member covering the second substrate, the electromagnetic shield member being made of metal; and an urging member configured to urge the substrate unit in a direction of causing the substrate unit to be close to the second frame, and to put the electromagnetic shield member into an electric conduction state by causing the electromagnetic shield member to abut on the second frame.

DETAILED DESCRIPTION OF THE PREFERRED EMBODIMENTS

Hereinafter, an embodiment of the present invention will be described with reference to the drawings.

Figure 1:
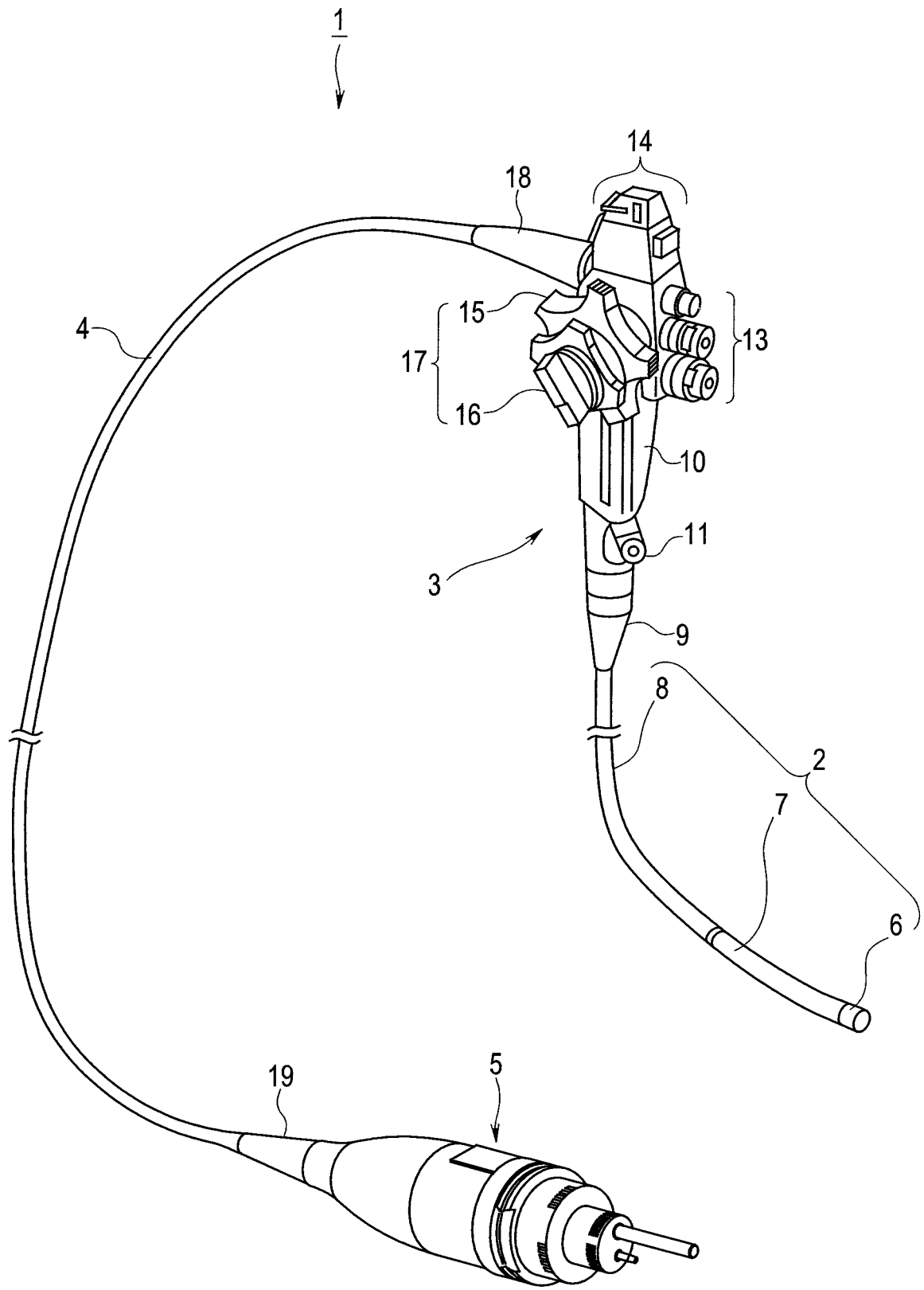
FIG. 1 is a perspective view showing a configuration of an endoscope in an embodiment of the present invention.
Figure 2:
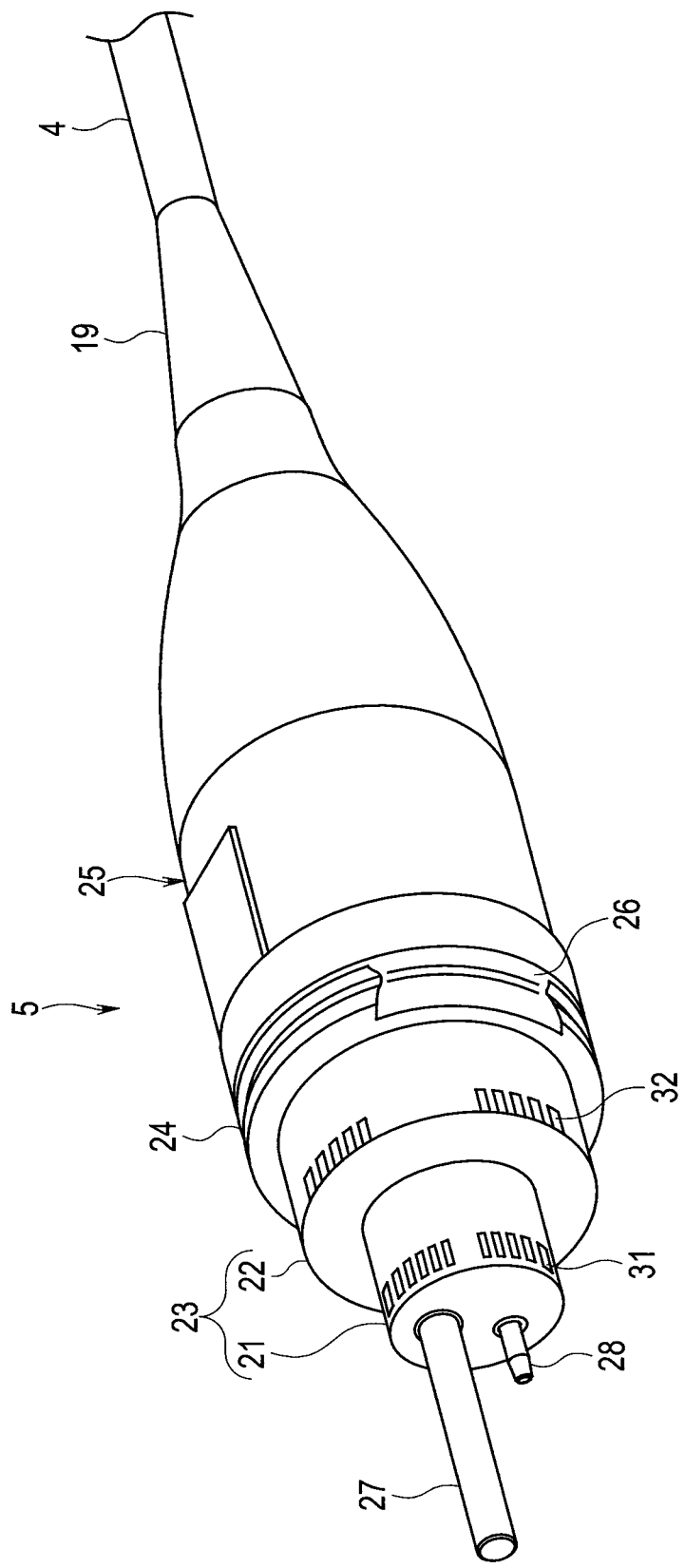
FIG. 2 is a perspective view showing a configuration of an endoscope connector in the embodiment of the present invention.
Figure 3:
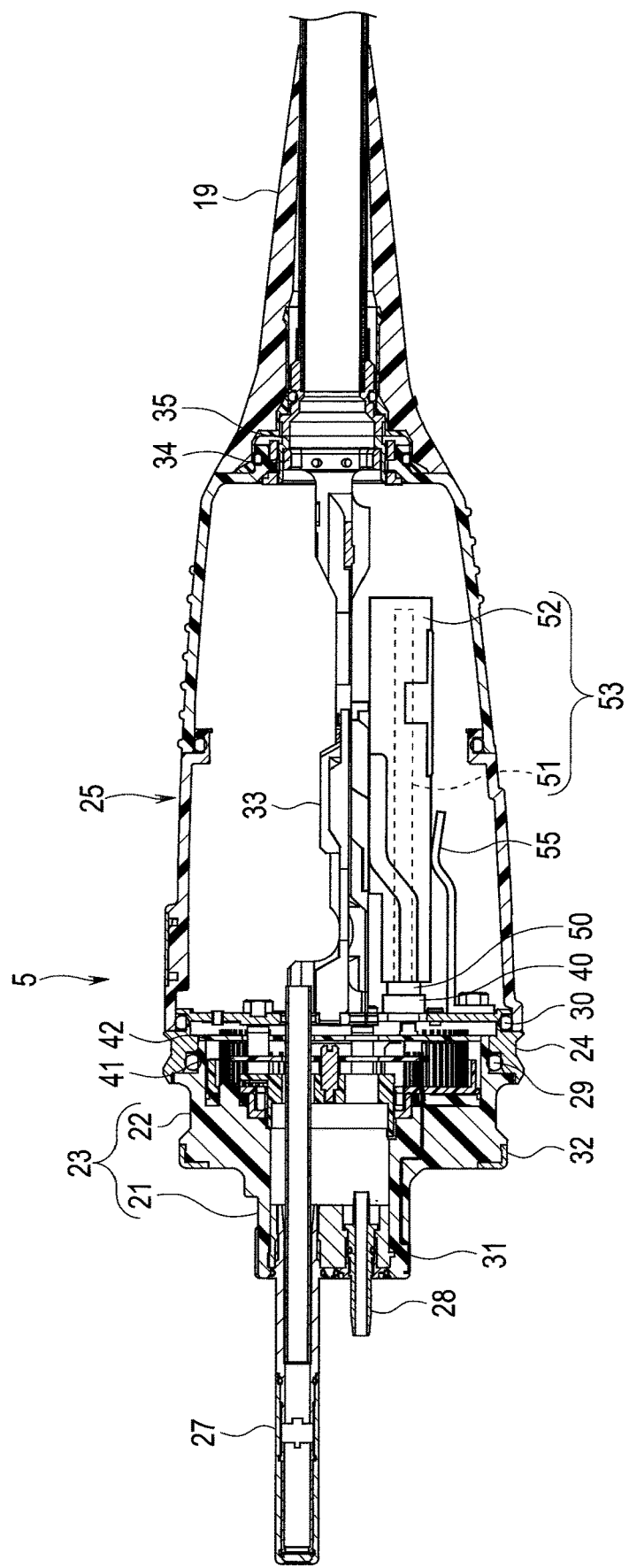
FIG. 3 is a sectional view showing the configuration of the endoscope connector in the embodiment of the present invention.
Figure 4:
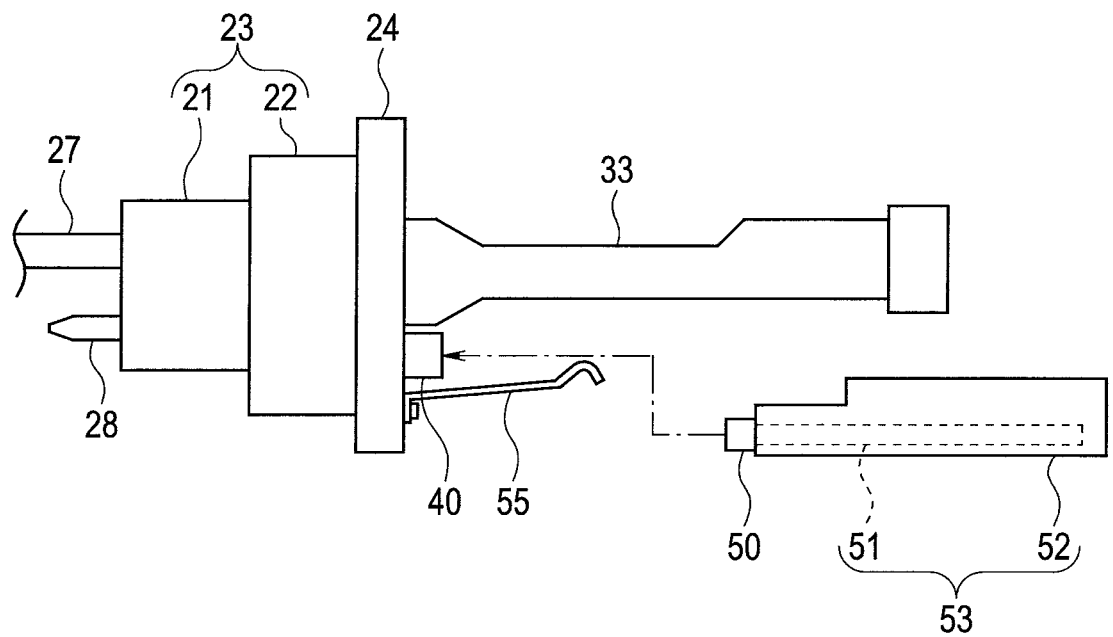
FIG. 4 is a diagram showing a state before a second board connector of a main-substrate unit is connected to a first board connector in the embodiment of the present invention.
Figure 5:
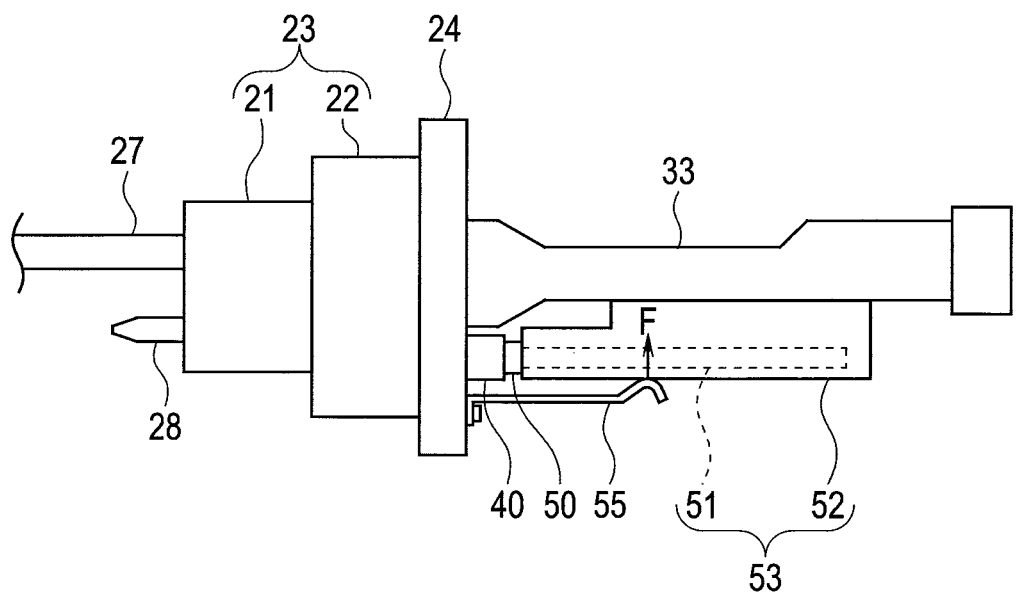
FIG. 5 is a diagram showing a state where the second board connector of the main-substrate unit has been connected to the first board connector in the embodiment of the present invention.

FIG. 1 is a perspective view showing a configuration of an endoscope, FIG. 2 is a perspective view showing a configuration of an endoscope connector, FIG. 3 is a sectional view showing the configuration of the endoscope connector, FIG. 4 is a diagram showing a state before a second board connector of a main-substrate unit is connected to a first board connector, and FIG. 5 is a diagram showing a state where the second board connector of the main-substrate unit has been connected to the first board connector.

In the respective figures that are used in following descriptions, in order that sizes of respective component elements are sizes allowing recognition in the figures, some scales are differentiated for each of component elements. The present invention is not limited only to quantities of the component elements, shapes of the component elements, size proportions of the component elements and relative position relations of the respective component elements that are described in the figures.

As shown in FIG. 1, an endoscope 1 in the embodiment includes an insertion portion 2 as an elongated long member configured to be inserted into an observation object site, herein into a lumen such as a large intestine, an operation portion 3 continuously provided at a proximal end portion of the insertion portion 2, a universal cable 4 that is a composite cable extending from a side surface of the operation portion 3, and an endoscope connector 5 that is a connector for medical apparatus configured to be connected to an external medical apparatus in a detachable manner. The external medical apparatus is a video processor (not illustrated) that is provided at an end portion of the universal cable 4 and is integral with a light source device.

The insertion portion 2 of the endoscope 1 includes a distal end portion 6 in which image pickup means is incorporated at a distal end side, and a bending portion 7 as a movable portion that is bendable is continuously provided at a rear portion of the distal end portion 6. Furthermore, a long flexible tube portion 8 that is formed of a tube-shaped soft member and that has flexibility is continuously provided at a rear portion of the bending portion 7. A proximal end portion of the flexible tube portion 8 of the insertion portion 2 is connected to a bend preventing portion 9 of the operation portion 3.

The operation portion 3 of the endoscope 1 includes a grasping portion 10 that is provided continuously with the bend preventing portion 9 and that is grasped by a user at time of use, and a treatment instrument insertion port 11 that configures a proximal end opening of a treatment instrument channel (not illustrated) arranged in the insertion portion 2 is provided at a coupling portion of the bend preventing portion 9 and the grasping portion 10.

On the grasping portion 10 of the operation portion 3, a bending operation portion 17 including two bending operation knobs 15 for performing a bending operation of the bending portion 7 of the insertion portion 2 and a fixing lever 16 for fixing the bending operation knobs 15 at desired rotational positions is arranged. Furthermore, switches 13, 14 for operating various endoscope functions are provided on the grasping portion 10.

Note that bend preventing members 18, 19 for maintaining connection strength and preventing damage due to a twist or the like are arranged on the universal cable 4 of the endoscope 1 so as to cover outer circumference portions at both end portions each connected to the operation portion 3 or the endoscope connector 5.

Next, the configuration of the endoscope connector 5 included in the endoscope 1 in the embodiment will be described below in detail.

Not that the endoscope connector 5 in the embodiment is arranged at a proximal end of the endoscope 1 that is an end part of the universal cable 4, and therefore, following descriptions will be made assuming that a side that is connected to the universal cable 4 is a distal end (front side) and a side that is connected to the external medical apparatus is a proximal end (rear side). Furthermore, the endoscope connector 5 is connected to an unillustrated external medical apparatus placed in an operation room, and therefore, following descriptions will be on the basis of a vertical direction that is determined in a state of being connected to the external medical apparatus.

First, as shown in FIG. 2, the endoscope connector 5 includes an electric plug portion 23, a flange portion 24 as a sub-frame (first frame), and an outer packaging case 25, in this order from a proximal end side. The electric plug portion 23 includes first and second electric connector portions 21, 22 that are formed as two-stage configuration, that have roughly columnar shapes with different outer diameters and that are integrally formed. The flange portion 24 is a disk-shaped frame connected to the second electric connector portion 22 of the electric plug portion 23 in a watertight manner. The outer packaging case 25 as a tube-shaped case body made of resin, which is connected to the flange portion 24 in a watertight manner and a diameter of which decreases toward the bend preventing member 19 on the universal cable 4 side.

On the first and second electric connector portions 21, 22, a plurality of electric contacts 31, 32 are respectively provided at parts of circumferential surfaces of outer circumference portions in a circumference direction in parallel.

Note that on an end surface (proximal end surface) of the first electric connector portion 21, a light guide pipe sleeve 27 that illumination light from the external apparatus enters is arranged on an upper portion side and an air feeding pipe sleeve 28 to which air from the external apparatus is fed is arranged on a lower portion side. Some outer packaging cases 25 are provided with a water feeding pipe sleeve, a front water feeding pipe sleeve, a suction pipe sleeve and the like, which are not illustrated here.

In the flange portion 24, both side portions of a metal disk member are cut out, and a rubber cover 26 that covers the cutout portion and that keeps insulation and watertightness is molded. Further, an O-shaped ring 29 (see FIG. 3) as a watertight member (sealing member) that contacts with an inner surface of the outer packaging case 25 and that keeps watertightness is provided on the flange portion 24. Note that the rubber cover 26 is also molded at a portion where the flange portion 24 abuts on an end surface of the outer packaging case 25 for keeping watertightness.

As shown in FIG. 3, a proximal end portion of a frame member 33 as a main-frame (second frame) is connected to a roughly central portion of the flange portion 24. A case fastening portion 34 having an annular shape is formed at a distal end portion of the frame member 33.

The outer packaging case 25 is attached so as to contain the frame member 33 and to abut on the flange portion 24. At this time, a fastening ring 35 configured to fix the outer packaging case 25 so as to compress the outer packaging case 25 toward the flange portion 24 side in a longitudinal direction is screwed to the case fastening portion 34 of the frame member 33.

The outer packaging case 25 is pressed against an O-shaped ring 30 as a watertight member (sealing member) that is provided at an outer circumference portion of the flange portion 24 and that keeps watertightness, and the connection to the flange portion 24 is kept in a watertight manner.

Plate-shaped sub-substrates 41, 42 having roughly circular shapes are provided in a space that is formed of the flange portion 24 and the electric plug portion 23. The sub-substrates 41, 42 are electrically connected to the plurality of electric contacts 31, 32 of the electric plug portion 23.

The sub-substrates 41, 42 are provided so as to project from an end surface on a distal end side of the flange portion 24, and are also electrically connected to a first board (substrate) connector 40 as a first electric connection member that is contained in the outer packaging case 25. Note that the first board connector 40 is arranged on the sub-substrate 42.

A second board (substrate) connector 50 as a second electric connection member provided on a main-substrate unit 53 is fit and electrically connected to the first board connector 40. The main-substrate unit 53 includes a plate-shaped main-substrate 51, and a shield box 52 as an electromagnetic shield member that is made of metal and that covers and contains the main-substrate 51.

Note that the sub-substrates 41, 42 and the main-substrate 51 process image pickup signals from an unillustrated image sensor that is provided at the distal end portion 6 of the insertion portion 2 or at the operation portion 3. The main-substrate 51 is electrically connected to an unillustrated communication cable. The communication cable extends from the shield box 52, and is inserted into the universal cable 4.

A plate spring 55 made of metal as an urging member is fixed to the flange portion 24 by a screw or the like. The plate spring 55 is an elastic member configured to perform surface contact between the shield box 52 and the frame member 33 by pressing the main-substrate unit 53 in a state where the second board connector 50 has been connected to the first board connector 40, onto the frame member 33. Note that the plate spring 55 is put into an electric conduction state by being fixed to the flange portion 24 made of metal.

In the endoscope connector 5 of the endoscope 1 in the embodiment, as shown in FIG. 4, when the main-substrate unit 53 is attached, the second board connector 50 is put and fit into the first board connector 40.

At this time, the main-substrate unit 53 is introduced between the frame member 33 and the plate spring 55. Then, the main-substrate unit 53 is urged to the frame member 33 side by the plate spring 55, while a surface on an opposite side of a surface facing the frame member 33 contacts with the plate spring 55.

In other words, the main-substrate unit 53 is gripped by the frame member 33 and the plate spring 55. In this state, as shown in FIG. 5, the main-substrate unit 53 constantly receives, from the plate spring 55, an urging force by which the main-substrate unit 53 is pressed to the frame member 33 side (pressed in an F direction indicated by an arrow in the figure).

In this way, the main-substrate unit 53 is arranged such that the shield box 52 made of metal abuts on the frame member 33 made of metal by the urge from the plate spring 55.

In other words, for the main-substrate unit 53, the electric connection with the sub-substrates 41, 42 is done by a B to B connector connection between the first board connector 40 and the second board connector 50.

The surface contact of the metal shield box 52 configured to abut on the plate spring 55 and to be urged to the frame member 33 side is actively made to the frame member 33 that is a metal frame, and thereby, the main-substrate unit 53 is stably put into an electric conduction state.

Furthermore, since the plate spring 55 made of metal is used, the shield box 52 of the main-substrate unit 53 is also put into an electric conduction state with the flange portion 24 made of metal through the plate spring 55.

In this way, the endoscope connector 5 has a configuration in which the shield box 52 can be stably put into an electric conduction state with the frame member 33 and the flange portion 24 by simply connecting and attaching the second board connector 50 of the main-substrate unit 53 to the first board connector 40 and ease of assembly is enhanced.

Note that the frame member 33 is electrically connected to a shield of a metal foil or metal net pipe of the universal cable 4 when the fastening ring 35 is screwed to the case fastening portion 34 at the distal end. The endoscope connector 5 is connected to the external medical apparatus such as a video processor, a light source device and the like, and thereby, the flange portion 24 is electrically connected to a patient ground that is provided in the external medical apparatus.

Accordingly, the endoscope connector 5 has a configuration in which the shield box 52 of the main-substrate unit 53 is electrically connected to the shield of the universal cable 4 and the patient ground of the external medical apparatus stably.

As described above, the endoscope connector 5 of the endoscope 1 makes it possible to stably put the frame member 33 having a large current-carrying capacity, the flange portion 24 and the shield box 52 of the main-substrate unit 53 into in an electric conduction state, and to suppress emission levels of electric waves and electromagnetic fields from the main-substrate 51 covered by the shield box 52, to values that meet EMC conformity items for medical apparatuses. Furthermore, the endoscope connector 5 of the endoscope 1 makes it possible to reduce influences of electric waves, electromagnetic fields and the like from an exterior to the main-substrate 51 of the main-substrate unit 53.

Thereby, the endoscope connector 5 makes it possible to enhance noise immunity, and also to reduce the number of parts because there is no need for a conventionally provided case-shaped shield member that covers internal components such as the frame member 33, the main-substrate unit 53 and the communication cable on an inner surface side of the outer packaging case 25.

From the above descriptions, the endoscope connector 5 included in the endoscope 1 in the embodiment makes it possible to increase noise immunity, to reduce the number of noise suppression components such as the case-shaped shield member, and to obtain effects of reduction in parts count and simplification of assembly.

Note that the elastic member (urging member) configured to urge the main-substrate unit 53 to the frame member 33, without being limited to the plate spring 55, may have a roughly clip-shaped form in which the frame member 33 and the main-substrate unit 53 are gripped or a form in which the frame member 33 and the main-substrate unit 53 are wound in a roughly rolling manner.

As described above, it is possible to realize the endoscope connector and the endoscope that make it easy to perform the electric connection of the substrate unit for noise immunity when the substrate unit is connected to the sub-substrate by the board-to-board connector, and that enhance ease of assembly.

The invention described in the above embodiment is not limited to the above embodiment, and in addition, various modifications can be made in an implementation phase without departing from the gist. Furthermore, the above embodiment includes inventions in various phases, and various inventions can be extracted by appropriate combinations in the plurality of constituent elements to be disclosed.

For example, even if some constituent elements are excluded from all constituent elements shown in the embodiment, the configuration in which the constituent elements are excluded can be extracted as an invention in the case where mentioned problems can be solved and mentioned effects can be obtained.

What is claimed is:

1. An endoscope connector comprising:
   a plug including an electric contact configured to be electrically connected to an external medical apparatus;
   a first substrate configured to be electrically connected to the electric contact;
   a first frame configured to be electrically connected to the plug;
   a second frame configured to be electrically connected to the first frame, the second frame being made of metal;
   a first electric connector configured to be electrically connected to the first substrate;
   a second electric connector configured to be electrically connected to the first electric connector;
   a substrate unit comprising:
     a second substrate configured to be electrically connected to the second electric connector; and
     an electromagnetic shield covering the second substrate, the electromagnetic shield being made of metal; and
   a biasing material formed separately from the second frame, the biasing material having a first surface configured to apply a biasing force to an opposing second surface of the substrate unit to bias the substrate unit towards the second frame to electrically connect the electromagnetic shield to the second frame.

2. The endoscope connector according to claim 1, wherein the biasing material is fixed to the first frame.

3. The endoscope connector according to claim 2, wherein the biasing material is a spring.

4. The endoscope connector according to claim 3, wherein the spring is a plate spring.

5. The endoscope connector according to claim 1, wherein the first frame is made of metal.

6. The endoscope connector according to claim 1, wherein the first electric connector and the second electric connector are substrate connectors.

7. The endoscope connector according to claim 1, further comprising a case body formed in a cylindrical shape, wherein the second frame, the first electric connector, the substrate unit and the biasing material are contained in a space defined by the case body and the first frame.

8. The endoscope connector according to claim 7, further comprising a seal disposed between an outer surface of the first frame and an inner surface of the case body.

9. The endoscope connector according to claim 8, wherein the seal is an O-ring.

10. An endoscope including the endoscope connector according to claim 1.

11. The endoscope connector according to claim 1, wherein the first electric connector is fit into the second electric connector.

12. The endoscope connector according to claim 1, wherein the electromagnetic shield of the substrate unit is electrically connected to the first frame through the biasing material.

13. The endoscope connector according to claim 1, wherein the plug comprising a first connector portion and a second connector portion, the second connector portion is disposed proximally relative to the first connector portion, an outer diameter of the first connector portion is smaller than an outer diameter of the second connector portion.

14. The endoscope connector according to claim 13, wherein the first frame is connected to the second connector portion in a watertight manner.

15. The endoscope connector according to claim 1, wherein the second substrate is accommodated in the electromagnetic shield.

16. An endoscope connector comprising:
   a plug including an electric contact configured to be electrically connected to an external medical apparatus,
   a first substrate configured to be electrically connected to the electric contact;
   a first frame configured to be electrically connected to the plug;
   a second frame configured to be electrically connected to the first frame, the second frame being made of metal;
   a first electric connector configured to be electrically connected to the first substrate;
   a second electric connector configured to be electrically connected to the first electric connector;
   a substrate unit comprising:
     a second substrate configured to be electrically connected to the second electric connector; and
     an electromagnetic shield covering the second substrate, the electromagnetic shield being made of metal; and
   a spring configured to bias the substrate unit in a direction of causing the substrate unit to be close to the second frame, and to put the electromagnetic shield into an electric conduction state by causing the electromagnetic shield to abut on the second frame.

\* \* \* \* \*